United States Patent
Kantor

(10) Patent No.: US 10,492,941 B2
(45) Date of Patent: Dec. 3, 2019

(54) AIRWAY SYSTEM WITH IMMOBILIZATION

(71) Applicant: INOVYTEC MEDICAL SOLUTIONS LTD., Hod Hasharon (IL)

(72) Inventor: Ehud Kantor, Hod Hasharon (IL)

(73) Assignee: Inovytec Medical Solutions Ltd., Hod Hasharon (IL)

( * ) Notice: Subject to any disclaimer, the term of this patent is extended or adjusted under 35 U.S.C. 154(b) by 402 days.

(21) Appl. No.: 14/912,425

(22) PCT Filed: Aug. 18, 2014

(86) PCT No.: PCT/IL2014/050741
§ 371 (c)(1),
(2) Date: Feb. 17, 2016

(87) PCT Pub. No.: WO2015/025319
PCT Pub. Date: Feb. 26, 2015

(65) Prior Publication Data
US 2016/0199211 A1 Jul. 14, 2016

(30) Foreign Application Priority Data

Aug. 19, 2013 (IL) .......................................... 228021

(51) Int. Cl.
*A61F 5/00* (2006.01)
*A61F 5/055* (2006.01)

(52) U.S. Cl.
CPC ..................... *A61F 5/055* (2013.01)

(58) Field of Classification Search
CPC .... A61F 5/055; A61F 5/05; A61F 5/04; A61F 5/05883; A61F 5/05891; A61F 5/37;
(Continued)

(56) References Cited

U.S. PATENT DOCUMENTS 3,477,425 A * 11/1969 Grassl ..................... A61F 5/055
128/DIG. 23
3,507,273 A * 4/1970 Yellin ..................... A61F 5/055
602/18
(Continued)

FOREIGN PATENT DOCUMENTS

EP          1738724 A1     1/2007

OTHER PUBLICATIONS

Lubovsky et al., A new external upper airway opening device combined with a cervical collar, Resuscitation 81 (2010) 817-821.
(Continued)

*Primary Examiner* — Victoria J Hicks
(74) *Attorney, Agent, or Firm* — Roach Brown McCarthy & Gruber, P.C.; Kevin D. McCarthy

(57) ABSTRACT

A cervical collar for ensuring an open airway has an occipital portion, right and left mandible engaging sections extending from the occipital portion, and right and left sternum engaging portions extending from the occipital portion. Each of the mandible engaging sections has an adjustable airway opening member for assuring opening of the airway. In one embodiment, each of the mandible engaging sections has a baseplate, and a carrier for the airway opening member which is controllably displaceable along a groove formed in the baseplate. A strap is attachable to an anterior portion of each baseplate, so that right and left straps are simultaneously tensionable and fastenable together on the chin of a subject to ensure symmetric stabilization. The anterior triangle of the neck is unobstructed following fastening together of the straps and of the sternum engaging portions, to facilitate monitoring of various throat related clinical conditions following a traumatic event.

17 Claims, 9 Drawing Sheets

(58) Field of Classification Search
CPC ........ A61F 5/3707; A61F 5/56; Y10S 128/23; A61G 13/1215; A61G 13/121; A61G 13/12
See application file for complete search history.

(56) References Cited

U.S. PATENT DOCUMENTS

| | | | |
|---|---|---|---|
| 5,048,509 A | 9/1991 | Grundei et al. | |
| 5,682,632 A | 11/1997 | Cotroneo | |
| 5,785,058 A | 7/1998 | Reynolds | |
| 7,128,724 B2* | 10/2006 | Marsh | A61F 5/055 602/18 |
| 7,674,234 B2 | 3/2010 | Calco et al. | |
| 7,981,068 B2 | 7/2011 | Thorgilsdottir et al. | |
| 8,262,596 B2 | 9/2012 | Gefen et al. | |
| 9,717,621 B2* | 8/2017 | Haider | A61F 5/055 |
| 2005/0113728 A1* | 5/2005 | Heinz | A61F 5/055 602/18 |
| 2011/0034844 A1 | 2/2011 | Thorgilsdottier et al. | |
| 2012/0186591 A1 | 7/2012 | Sethi et al. | |
| 2013/0281900 A1* | 10/2013 | Suarez | A61F 5/055 602/18 |

OTHER PUBLICATIONS

International Search Report for a counterpart foreign application—PCT/IL2014/050741—2 pages, dated Nov. 19, 2014.
Written Opinion of the International Searching Authority for a counterpart foreign application—PCT/IL2014/050741—6 pages, dated Nov. 19, 2014.
International Preliminary Report on Patentability with notification of transmittal of International Preliminary Report on Patentability for a counterpart foreign application—PCT/IL2014/050741—14 pages, dated Dec. 22, 2015.
A communication (office action) from a foreign patent office (India) in a counterpart foreign application (No. 201617009093), dated Sep. 19, 2019, 6 pages.

* cited by examiner

AIRWAY SYSTEM WITH IMMOBILIZATION

FIELD OF THE INVENTION

The present invention generally relates to a non-invasive airway protector that stabilizes the cervical spine. More particularly, the invention relates to a cervical collar that facilitates monitoring of the throat following a traumatic event.

BACKGROUND OF THE INVENTION

The human spine comprises some vertebrae grouped into three sections according to location: cervical spine (neck), thoracic spine (middle back), and lumbar spine (lower back). Soft tissues, including ligaments, muscles, and skin, surround and support the spine. Seven of the vertebrae form the cervical spine connecting the base of the head to the thorax (trunk and shoulders) and supporting the head.

In the practice of emergency medicine and the treatment of trauma, when damage to the cervical spine in suspected, there is often a need to secure the head and neck of a patient, to prevent movement of the cervical spine vertebrate and deterioration of the patient's condition. Spinal cord damage can result in partial or complete paralysis or even death.

Cervical collars are a common protective device well known in the medical art. In the treatment of spinal cord damage it is common to perform x-ray or similar imaging of the damaged area. Therefore cervical collars are often made of materials transparent to x-rays. Cervical collars are additionally often required to be lightweight and comfortable, and also to be cheap and easy to manufacture.

Furthermore, in the practice of emergency medicine and the treatment of trauma it is common for a patient to loose consciousness and the ability to maintain open airways and respiration. Loss of respiration is often fatal. There are several methods known in the art for maintaining open airways. All invasive methods to maintain an open airway involve devices that are inserted into the airway and mechanically supply an open tube aimed to maintain an open airway. One invasive technique is surgical cricothyroidotomy involving the insertion of a tube through the neck of the patient. Other invasive techniques involve tracheal intubation or laryngeal mask. The non-invasive way to protect the airway in trauma patients is by manually pushing the jaw forward.

There is therefore a need simultaneously to protect the spine and maintain open airways, as both conditions, damage to the spine and suffocation, are highly damaging, often fatal, and usually irreversible. Therefore there is a need for cervical collars to enable opening of the airways. It is thus common for cervical collars to comprise a hole or an opening in the region of the front of the neck to allow invasive techniques such as surgical cricothyroidotomy. It is well recognized in the literature that cervical collars, not only do not support the opening of the airway, but also compromise airway flow, a condition that sometimes necessitates to compromise the spine control, and open the anterior part of the collar in order to enable adequate airway.

There are techniques known in the art for maintaining open airways by maintaining an open mouth. Being less invasive than perforating the neck, they are usually preferable. However, the need to open the mouth of a patient tends to conflict with the requirement of maintaining a rigid position of the head to prevent damage to the spine. There are techniques known in the art for opening the mouth while minimizing other motion of the head. Such techniques include several variations on the jaw thrust maneuver.

Various patents show means for immobilizing the head of injured patients. U.S. Pat. No. 5,048,509 discloses a cervical support that has an inherently stable support body of elastic foam material, and a jaw support regions which extend symmetrically and in mirror image relationship with respect to an imaginary longitudinal axis connecting the centers of the nape support region and the chin support region. This collar constructed from two parts is adapted to be mutually assembled rigidly, without effective means of maneuvering mandible-clasping members of the collar. Similarly, U.S. Pat. No. 5,785,058 teaches a disposable head and neck immobilization device allows reducing contamination hazard from transfer of bodily fluids. The mandible is effectively fastened by means of said collar, yet airway maintenance is not provided. Both devices do not inherently promote open airway, and actually can generate force in vector opposite to the needed one that acts to close the airway. Both patents do not maintain the jaw forward continually and thus they not protect the airway.

U.S. Pat. No. 5,682,632 presents a head rest device for use under a patient's head, the device comprising a base and a jaw thrust support having at least two protuberances extending upward from the upper surface of the base for engaging with the patient's mandible at angles of the mandible so that the patient's mandible is thrust out distracting the patient's tongue and associated structures in a direction away from the patient's head and neck, and in so doing, opening the patient's oropharynx and hypopharynx and lifting the patient's epiglottis out from in front of the patient's laryngeal inlet. Using this device, the patient's head rest in a hyperextended position that is dangerous for his cervical spine and is totally contraindicated in trauma patients. Moreover this device does not protect and stabilize the cervical spine.

U.S. Pat. No. 8,262,596 discloses a cervical collar for maintaining open airways that comprises a posterior part that is placed behind the head of a patient, an anterior part fit in front of the patient's neck and attached to the posterior part to define a motion-restricting frame, and a jaw clasp for performing a jaw thrust maneuver that is connected to the frame. As the patient's neck is covered by the anterior part, visualization of the throat during a traumatic event is not possible, seriously reducing the number of treatment possibilities that a health practitioner can take in trying to improve the well being, or even to save the life, of the patient.

It is an object of the present invention to provide a cervical collar that facilitates both opening of the airway as well as monitoring of the throat following a traumatic event.

Other objects and advantages of the invention will become apparent as the description proceeds.

SUMMARY OF THE INVENTION

The present invention provides a cervical collar for ensuring an open airway, comprising an occipital portion, right and left mandible engaging sections extending from said occipital portion, and right and left sternum engaging portions extending from said occipital portion, wherein each of said mandible engaging sections comprises an adjustable airway opening member for assuring opening of the airway.

The anterior triangle of the neck is unobstructed when the right and lefts straps are fastened together and when the right and left sternum engaging portions are fastened together, to thereby facilitate monitoring of various throat related clinical conditions following a traumatic event.

In one aspect, the cervical collar is a unitary member with an integrated jaw clasp in the form of the airway opening member. The cervical collar is adjustable to fit the neck and face sizes of most people. Manufacturing costs are reduced as the occipital portion and the sternum engaging portions are formed in a single panel.

In one aspect, each of the mandible engaging sections is pivotal about a corresponding axle fixed to the occipital portion in order to facilitate engagement with the mandible.

In one aspect, each of the mandible engaging sections comprises a baseplate and a carrier for the airway opening member which is controllably displaceable along a groove formed in said baseplate. The carrier may be longitudinally and ratchetedly displaceable along the groove, being connected to a manipulator by a fastening element passing through the groove. The airway opening member protrudes medially from the baseplate and the manipulator protrudes distally therefrom.

The airway opening member is an external airway device that applies a force onto the corresponding mandible angle to push the mandible forwardly and to cause the jaws to open, thereby preventing backward collapse of the mandible and suffocation.

The airway opening member comprises a first element for contacting the bottom of the mandible angle and a second element which is angularly spaced and extends upwardly from said first element, for example by an angle ranging from 110 to 160 degrees.

The airway opening member supports the mandible in two directions. As it supports the mandible from below, the airway opening member prevents flexion of the neck, thus stabilizing the cervical spin. As the airway opening member applies a force onto the mandible angle from behind, it induces forward movement of the mandible to enable opening of the airway while continuing to prevent flexion movement of neck. Since the vector that prevents flexion is applied to the mandible by the airway opening member from both sides, the front of the collar is open for wide visualization of the neck.

The panel is preferably of bilateral symmetry. The right and left sternum engaging portions are simultaneously tensionable and fastenable together to ensure symmetric stabilization.

In one aspect, the panel is configured with two portions contiguous with a corresponding sternum engaging portion and between which the occipital portion is interposed, for engaging, when tensioned, the sternocleidomastoid muscle, to prevent sideways head movement.

In one aspect, the cervical collar further comprises a strap attachable to an anterior portion of each baseplate, wherein said right and left straps are simultaneously tensionable and fastenable together on the chin of a subject to ensure symmetric stabilization.

DETAILED DESCRIPTION OF PREFERRED EMBODIMENTS

The novel cervical collar of the present invention that is able to reliably immobilize a subject's neck in a trauma situation, yet facilitates opening of the airway for example by the jaw thrust maneuver and enables a medical practitioner to monitor clinical conditions of the anterior triangle of the neck.

While prior art cervical collars are comprised of several sections that need to be coupled together and adjusted by a practitioner standing at the side of the subject, potentially resulting in asymmetrical stabilization of the neck that is liable to permit life threatening movement of the cervical spine vertebrate, the cervical collar of the present invention is engaged onto the subject by a practitioner standing at the subject's front who simultaneously manipulates right and left engagement elements to ensure symmetrical stabilization of the neck and head.

Figure 1:
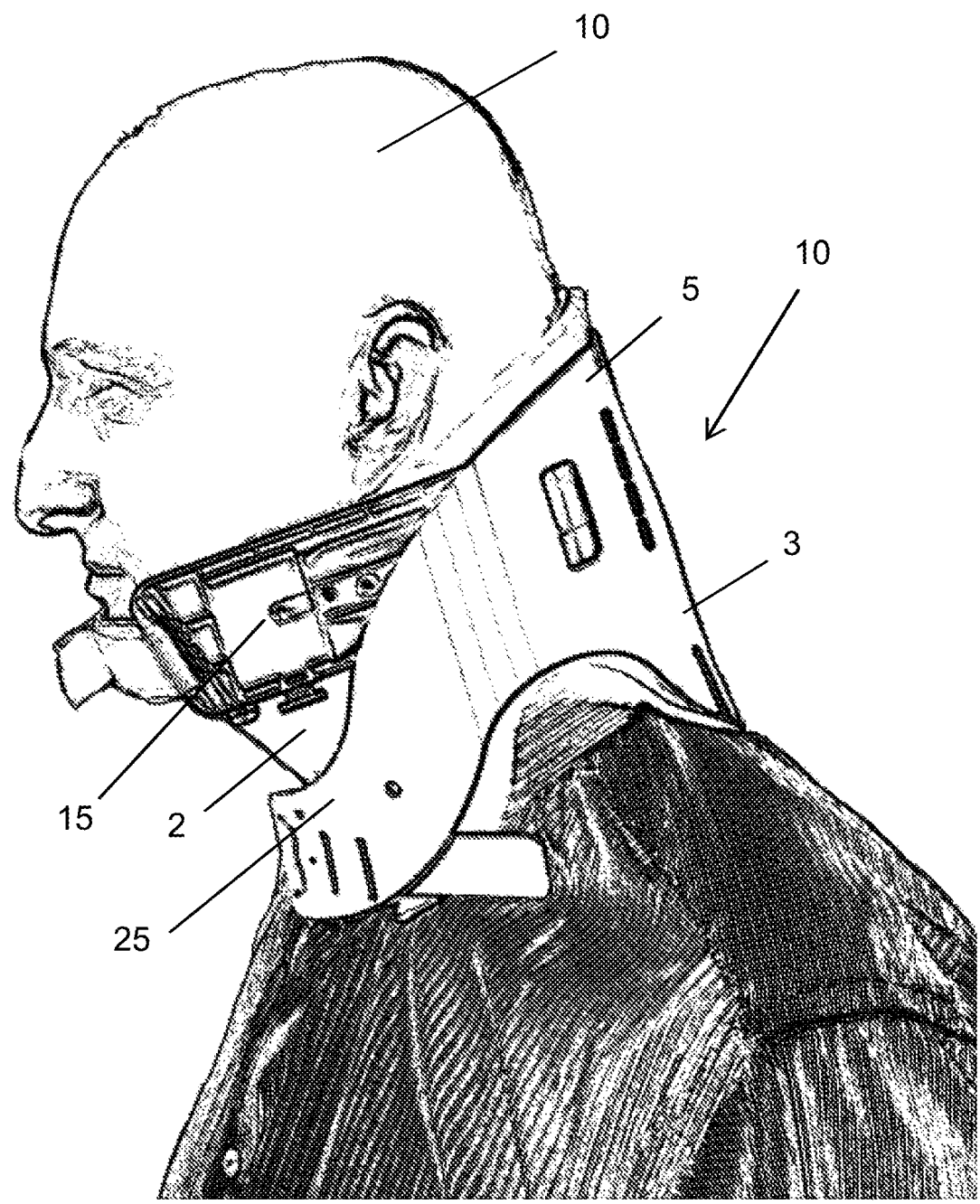
FIG. 1 is a side view of a cervical collar, according to one embodiment of the present invention, when positioned in neck stabilizing engagement with a subject.

FIG. 1 illustrates a cervical collar generally indicated by numeral 10, according to one embodiment of the invention, when in neck stabilizing engagement with subject 1.

Cervical collar 10 is a unitary member which is adjustable to fit the neck and face sizes of most people. Cervical collar 10 comprises a flexible panel 3 forming an occipital portion 5 and left and right sternum engaging portions 25 when bodily engaged as shown. Left and right mandible engaging sections 15 are pivotally connected to panel 3. The mandible engaging sections 15 and the sternum engaging portions 25 are adjustable to ensure proper body engagement while exposing the anterior triangle 2 of the neck Reference is now made to FIG. 2, which illustrates the anterior face of panel 3 when flattened out and when mandible engaging sections are removed, for purposes of clarity.

Panel 3, which has bilateral symmetry with the exception of fastening strip 36, is made from any suitable flexible and non-irritating material, such as soft foam material, natural and synthetic polymers, and metal wire reinforced materials, which can comfortably conform to the bodily portions when bent and remain engaged for prolonged periods of times without causing decubitis or other types of irritation. An element designated by the letter R will indicate one located on the right side of the subject, and an element designated by the letter L will indicate one located on the left side of the subject.

An intermediate region 4 of panel 3 is defined by an upper, slightly curved edge 7 and a lower convex edge 9 having a significantly greater curvature than upper edge 7. Intermediate lower edge 9 terminates at each side with a concave lower edge 11 to delimit the corresponding, considerably thinner sternum engaging portion 25, which is also defined by an L-shaped laterally extending edge 8 that extends from a corresponding side of intermediate upper edge 7. A plurality of laterally spaced, sagittally oriented slits 28 extend from each of edges 7 and 9 to facilitate flexing of panel 9 and resulting body conformity when being engaged.

Figure 8:
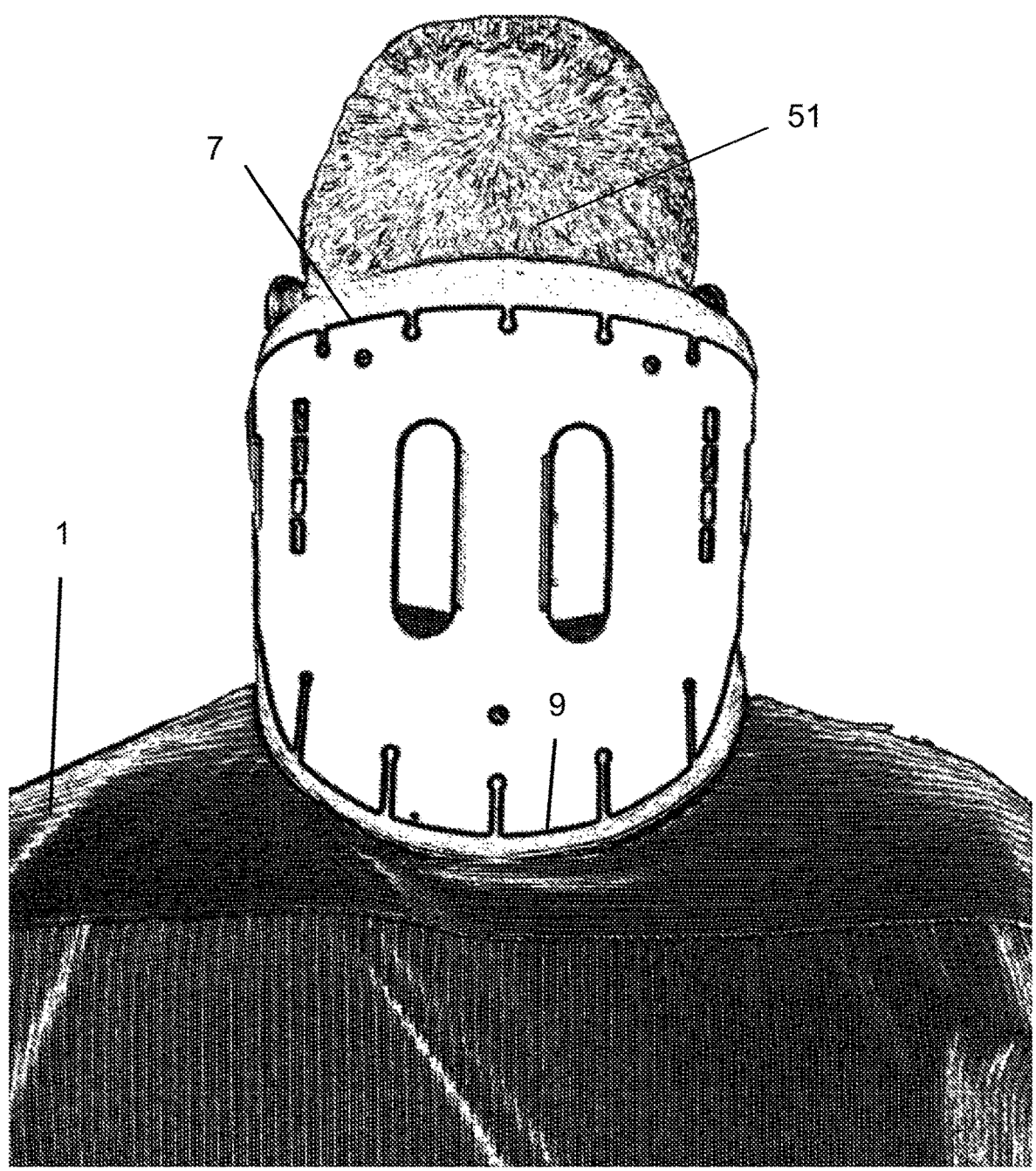
FIG. 8 is a rear view of the cervical collar of FIG. 1, when positioned in neck stabilizing engagement with a subject.

Intermediate region 4 includes central occipital portion 5 for engaging the occipital bone as shown in FIG. 8 and two SCM portions 19 between which occipital portion 5 is interposed for engaging the sternocleidomastoid (SCM) muscle at the side of the neck. The border 27 between portions 5 and 19 and intersecting concave lower edge 11 is schematically indicated by a dashed line, although the border will be different for each subject, depending on the subject's size and clinical condition.

Two oval ventilation apertures 6 are formed in occipital portion 5, and a rectangular ventilation aperture 26 is located in a corresponding SCM portion 19, substantially centrally located between the upper and lower edges. Two sagittally oriented axles 13, about which a mandible engaging section is able to pivot, are fixed to panel 3 within occipital portion 5, one adjacent to a corresponding border 7.

Each sternum engaging portion 25 is continuous with a corresponding SCM portion 19, with its upper convex edge 31 and lower convex edge 33, which has a substantially similar curvature as upper edge 31, extending from edges 8 and 11, respectively. The convex upper edge 31 of the respective sternum engaging portion 25 extends continuously from the corresponding L-shaped edge 8. The concave lower edge 11 of the corresponding SCM portion 19 extends continuously from the convex lower edge 9 of the occipital portion 5 to the convex lower edge 33 of the respective sternum engaging portion 25. This unique shape of sternum engaging portion 25 configured with concave edges 8 and 31 ensures that the two portions 25 will be coupled together and fixated at the rigid sternum and below the anterior triangle of the neck.

Figure 2:
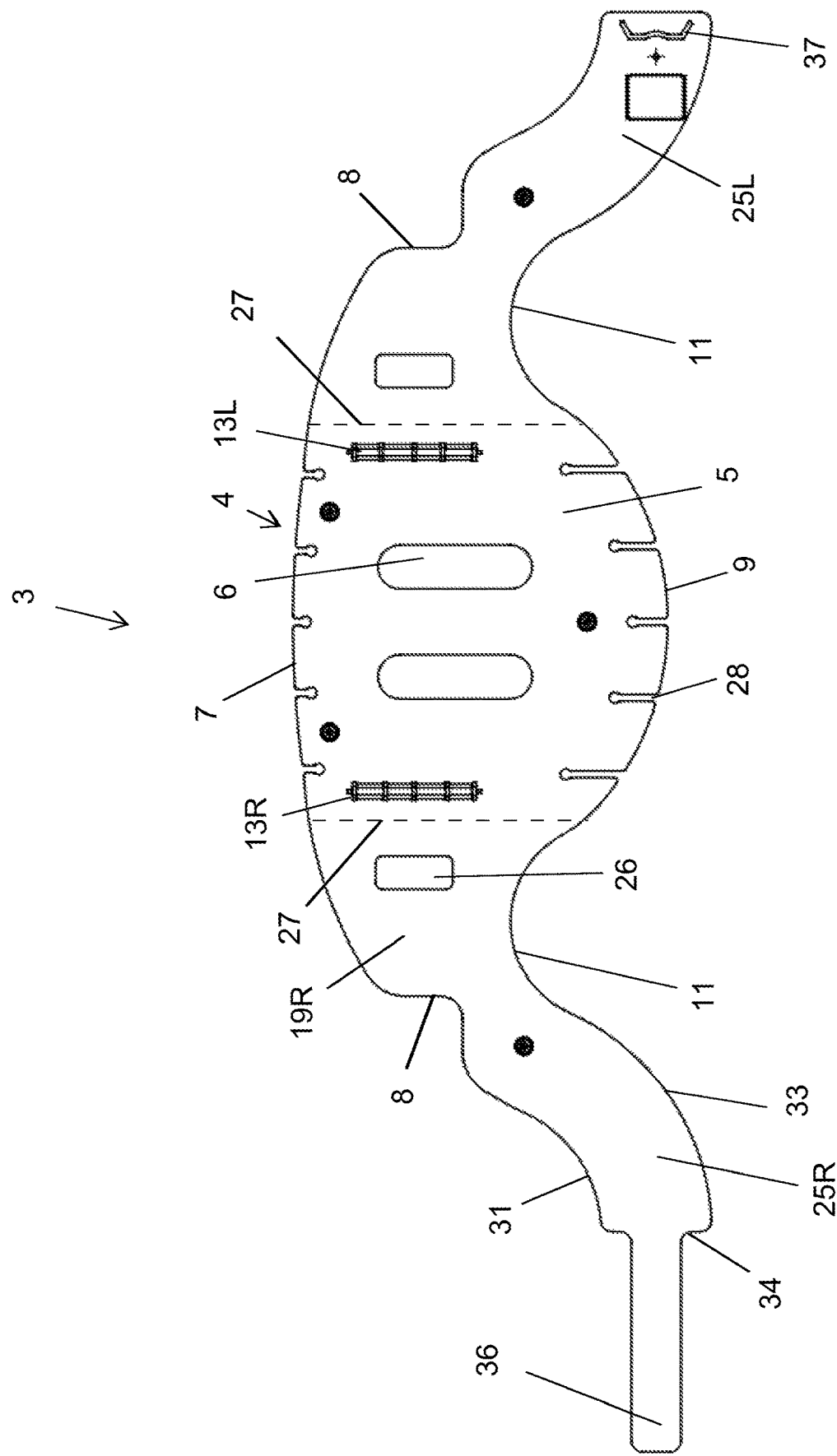
FIG. 2 is an anterior view of a panel used in conjunction with the cervical collar of FIG. 1, when flattened out and when mandible engaging sections are removed.

In order to couple together the two portions 25, the right sternum engaging portion 25R is provided with an elongated fastening strip 36 extending from a central portion of the lateral end 34 of portion 25R, and the left sternum engaging portion 25L is formed with a plurality of laterally spaced slits 37, only one of which being shown in FIG. 2. Fastening strip 36 is introducible into one of the slits 37 that provide suitable fixation of the cervical collar.

It will be appreciated that sternum engaging portions 25 may be provided with any other suitable fastening means including, but not limited to, straps, releasable adhesion means, hook and loop material, snaps, buttons and hooks.

Figure 3:
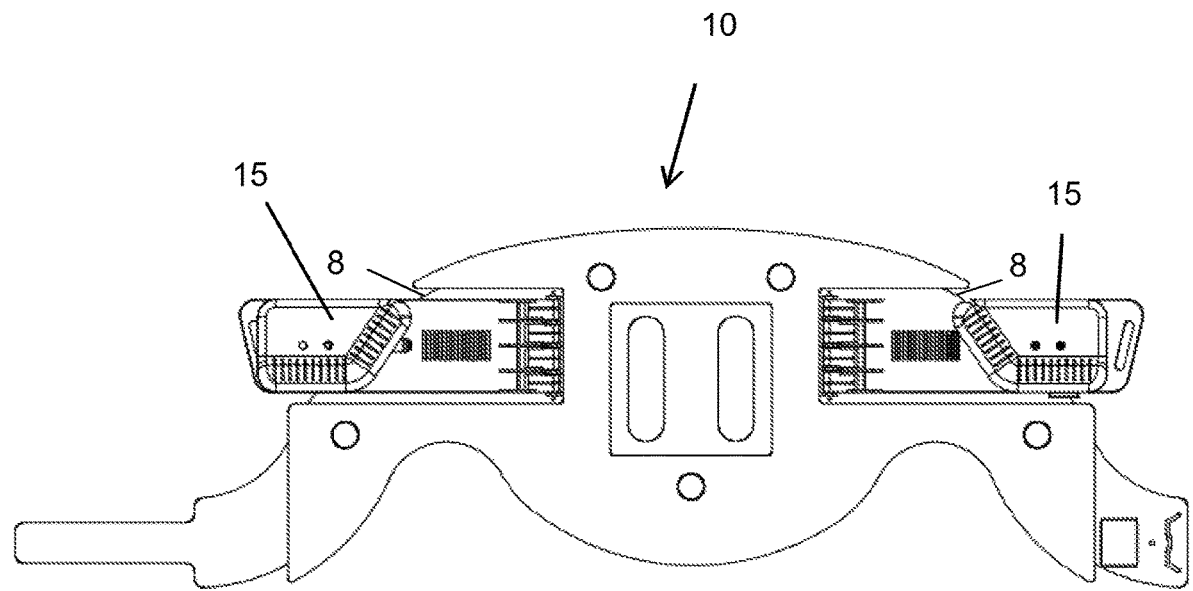
FIG. 3 is an anterior view of the cervical collar of FIG. 1, when not bodily engaged.

FIG. 3 illustrates an anterior view of an assembled cervical collar 10, when the panel is flattened out. As shown, the two mandible engaging sections 15 protrude laterally from a corresponding L-shaped edge.

Figure 4:
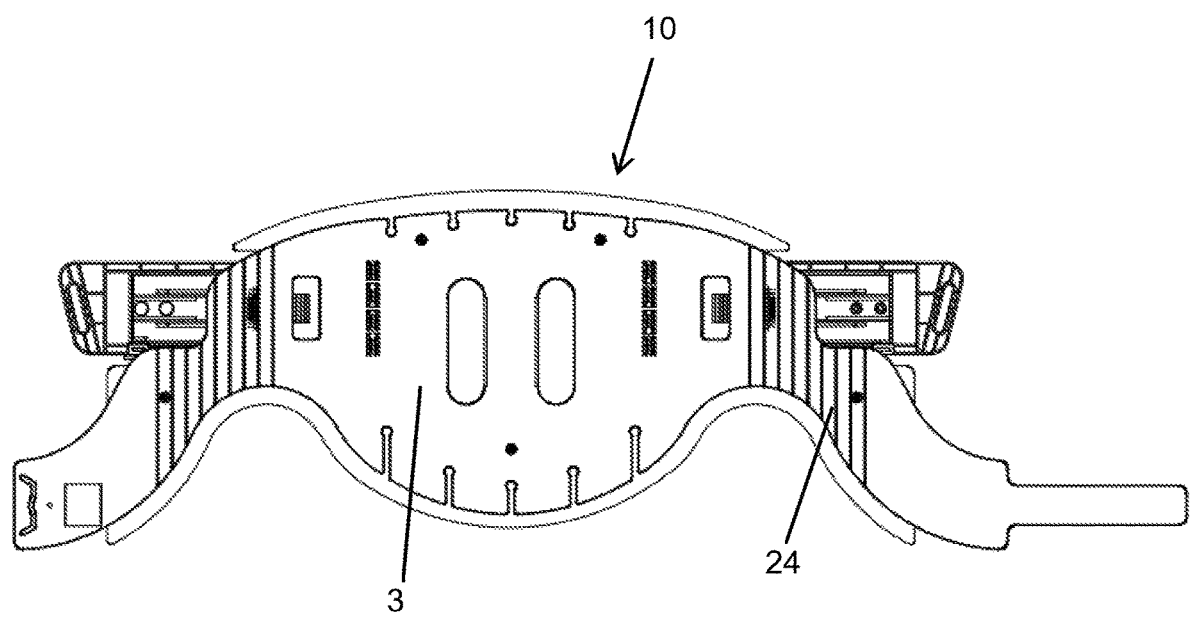
FIG. 4 is a posterior view of the cervical collar of FIG. 1, when slightly folded and not bodily engaged.

FIG. 4 illustrates a posterior view of cervical collar 10, showing fold lines 24 that are formed in the SCM portions, to assist in folding and bodily engaging panel 3.

Figure 5:
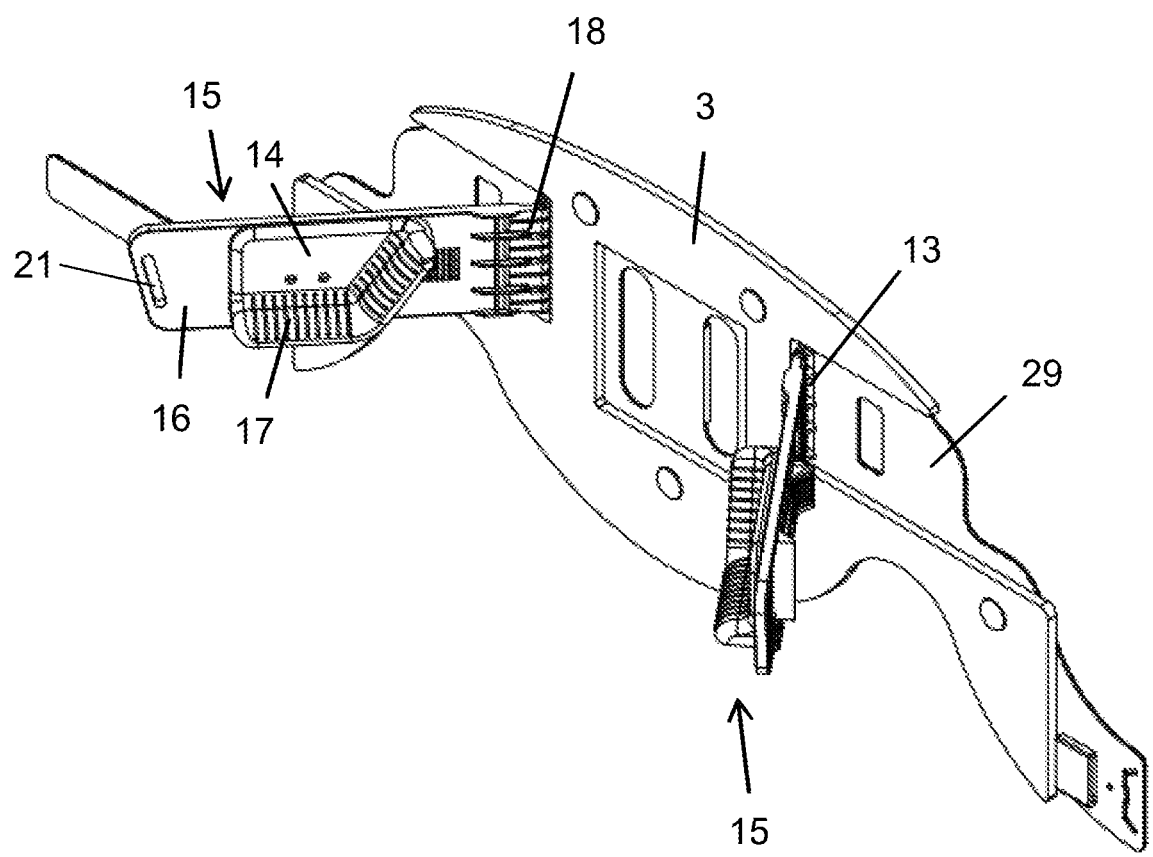
FIG. 5 is an anterior view of the cervical collar of FIG. 1, when the mandible engaging sections are in a pivoted position with respect to a flattened panel.

FIG. 5 illustrates cervical collar 10 when the mandible engaging sections 15 are in a pivoted position with respect to a flattened panel 3. Panel 3 is shown to be formed with a recess 29 in those areas of the SCM portion and the sternum engaging portion that coincide with a corresponding mandible engaging section 15 when panel 3 is flattened out, for compact storage. When cervical collar 10 is folded and bodily engaged, mandible engaging section 15 is once again received in recess 29.

In addition to the pivoting enabling components 18, mandible engaging section 15 comprises baseplate 16, which is pivotal about axle 13, trapezoidal carrier 14 which is longitudinally and adjustably displaceable along the medial side of baseplate 16, and angled airway opening member 17 protruding from carrier 14. A strap 23 (FIG. 9) applied with a fastening element, e.g. made of hook and loop material, is attachable to mandible engaging section 15 within an aperture 21 formed in each baseplate 16.

Although baseplate 16 is described as having a "medial" side and a "distal" side for describing a relative location when mandible engaging section 15 is bodily engaged, it is to be noted that these or other directional terms are also relevant to describe relative locations when mandible engaging section 15 is not bodily engaged.

Figure 6:
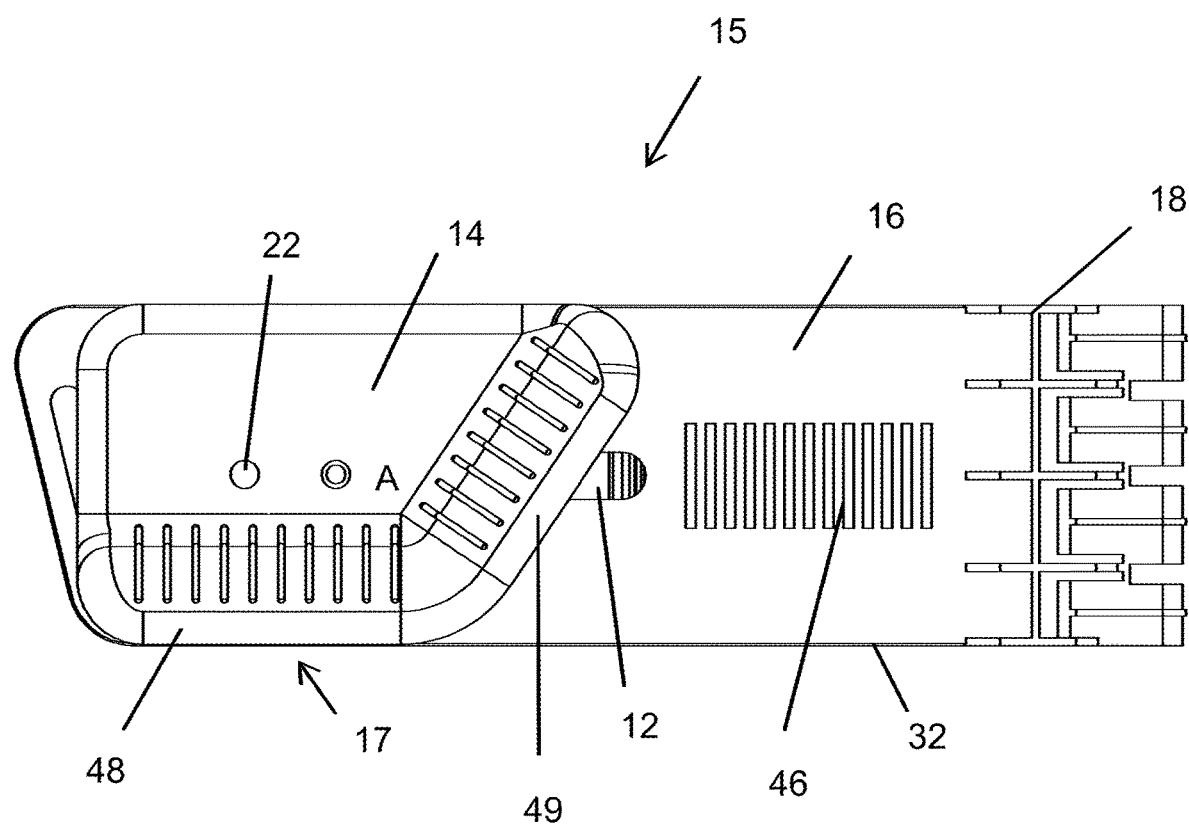
FIG. 6 is an enlarged distal view of the mandible engaging section of FIG. 5.
Figure 7:
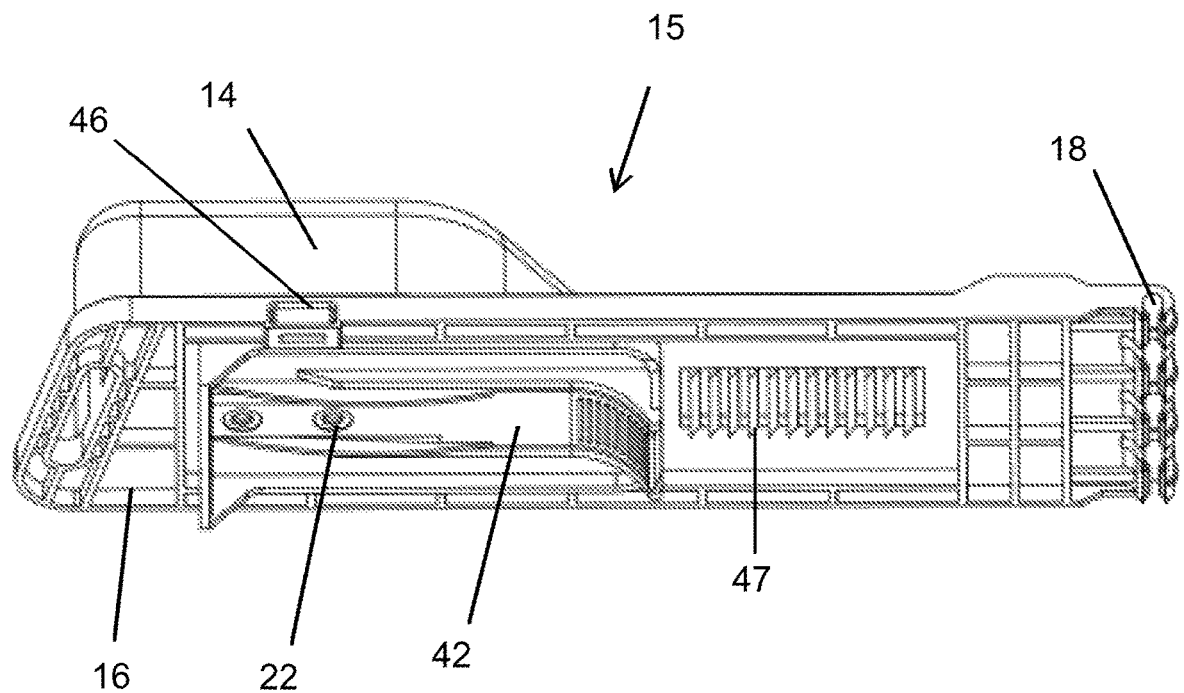
FIG. 7 is a perspective medial view of the mandible engaging section of FIG. 5.

The structure of mandible engaging section 15 is shown more clearly in FIGS. 6 and 7. Baseplate 16 is formed with a longitudinal groove 12, e.g. oval, along which carrier 14 is incrementally and anteroposteriorly displaceable. Two, or any other number of, fastening elements 22, which connect carrier 14 to manipulator 42 protruding from the distal side of baseplate 16, e.g. a curved handle, pass through groove 12 to enable the longitudinal displacement of carrier 14. Formed on baseplate 16 between groove 12 and pivoting enabling components 18 is an array 46 of teeth 47. Teeth 47 protrude distally from baseplate 16 and are angled in a uniform direction, so that a suitable element of manipulator 42 will engage the teeth to permit controllable and adjustable displacement in only one direction. A disengagement element 46 protruding upwardly from manipulator 42 is used to disengage manipulator 42 from the array of teeth, so that carrier 14 can be displaced in an opposite longitudinal direction.

Airway opening member 17 medially protruding from carrier 14 has a first substantially horizontal element 48 that is substantially parallel to bottom edge of baseplate 16 and a second element 49 angled upwardly from first element 48. Obtuse angle A between first element 48 and second element 49 ranges from 110-160 degrees. This angle is sufficient to cause, when airway opening member 17 is engaged with the angle of the mandible in the vicinity of the ramus, at a corresponding distal end of the mandible, the jaws to open for ensuring an open airway. Obtuse angle A between first element 48 and second element 49 constitutes an unoccupied interior space within which the corresponding mandible angle proximate to a junction with a ramus is receivable. First element 48, when supporting the bottom of the mandible angle, also serves to prevent downward tilt or flexion of the neck.

Figure 9:
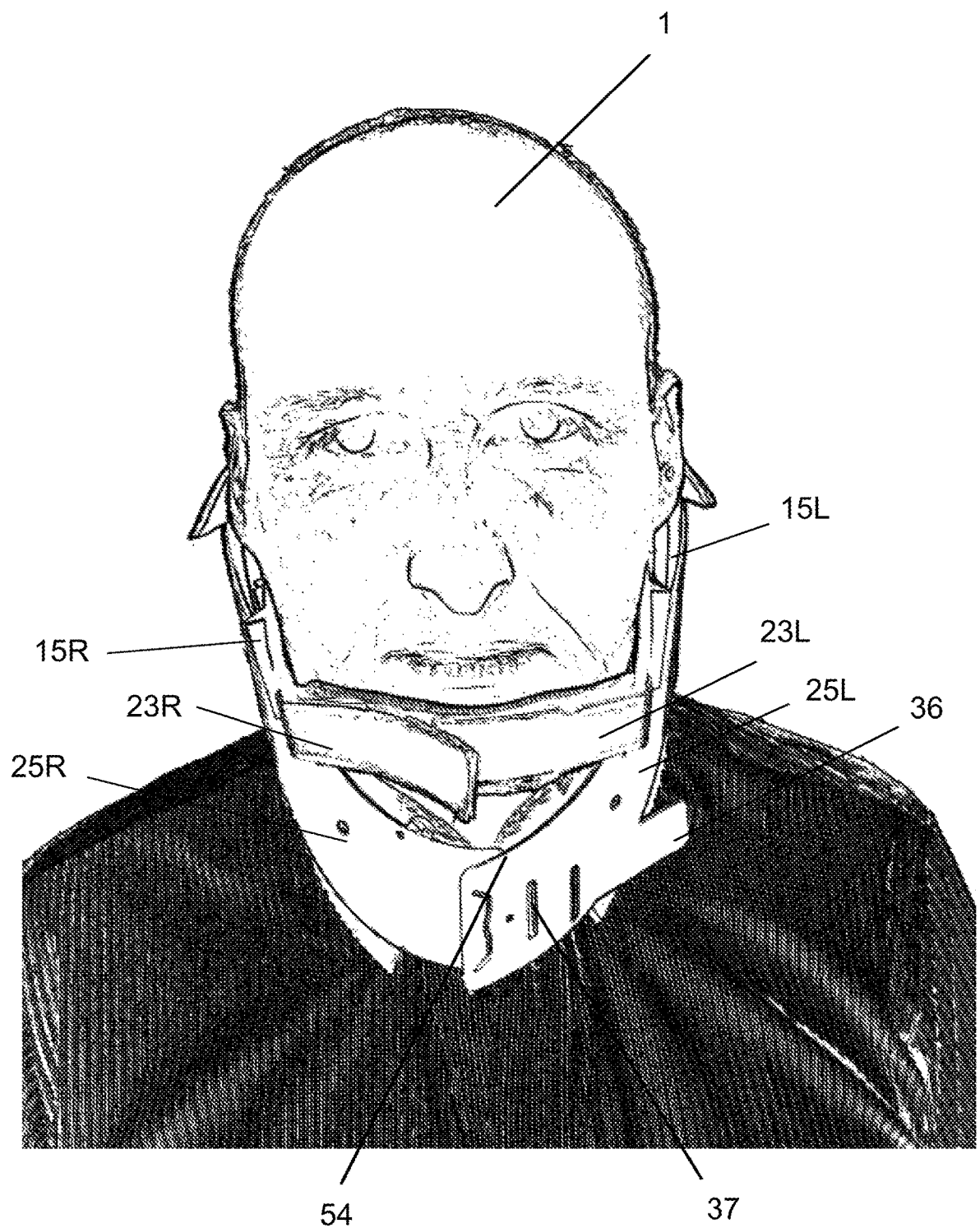
FIG. 9 is a front view of the cervical collar of FIG. 1, when positioned in neck stabilizing engagement with a subject.

In operation with reference to FIGS. 8 and 9, occipital portion 5 is first positioned to be centered and placed in engagement with the occipital bone 51 of the skull. Occipital portion 5 may be positioned when subject 1 is in a sitting position as shown, or alternatively may be positioned when the subject is in a supine position following for example a trauma situation when excessive movement of the cervical spine is liable to lead to paralysis. The distance between upper edge 7 and lower edge 9 of occipital portion 5 is sufficiently great to ensure that lower edge 9 will contact the upper back. Accordingly, when a sufficient tensile force is applied at the top of occipital portion 5 by the two mandible engaging sections 15 and by the two sternum engaging portion 25, rearward head motion is prevented.

A practitioner standing at the front of subject 1 then pulls on both sternum engaging portions 25 simultaneously until they are tensed and inserts fastening element 36 into the selected slit 37 that will ensure that the junction 54 between portions 25R and 25L will be in engagement with the rigid sternum, located below the soft tissues of the anterior triangle of the neck.

Each carrier 14 of mandible engaging section 15 is manipulated until airway opening member 17 contacts the corresponding mandible angle, after the latter has been received within the unoccupied interior space of the airway opening member. The right and left straps 23R and 23L are then simultaneously pulled, while the SCM portions are tensed, to ensure that airway opening member 17 applies a force on the corresponding mandible angle for causing the jaws to open and the airway to remain opened. Although the lips of subject 1 appear to be closed, this lip position does not preclude the possibility of the jaws being opened since a jaw opening of even one centimeter is sufficient to ensure an open airway.

The right and left straps 23R and 23L are then pivoted and fastened together, ensuring that they will remain engaged onto the chin of the subject. Forward head movement is thereby prevented since the occipital portion is in engagement with the back of the head and the straps are in engagement with the chin. Sideways head movement is also prevented since each SCM portion is in engagement with a corresponding SCM muscle, which runs downwardly along the side of the neck substantially below the ear and functions to rotate or extend the head.

Simultaneous fastening of the straps 23 together and simultaneous fastening of the sternum engaging portions 25 together ensures that the head and neck will be assured of being symmetrically stabilized.

As the structure of the aforementioned cervical collar ensures that the anterior triangle of the neck located between the two SCM muscles remains exposed, as described hereinabove, a medical practitioner is able to monitor various clinical conditions, after the cervical collar has been bodily engaged, which have not been observable heretofore by prior art cervical collars which cover a significant amount of the anterior triangle in order to provide sufficient head immobility.

Exemplary clinical conditions that are observable by the cervical collar of the present invention are visualization of the thyroid cartilage to monitor breathing and swallowing patterns, measuring blood pulse in the carotid artery, visualization of bleeding or swelling in the anterior triangle, monitoring subcutaneous bleeding, and visualizing an expanding neck hematoma.

An exposed anterior triangle also enables a member of an intensive care unit to perform a tracheostomy to invasively open the airway of a neck stabilized subject, or to perform a transfusion via the external jugular vein.

All of these advantages are achievable by a collar that is surprisingly light, easily and quickly manipulated, and of superior neck stabilization.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A cervical collar for ensuring an open airway of a subject, comprising an occipital portion, right and left mandible engaging sections extending from said occipital portion, and separate right and left sternum engaging portions extending from said occipital portion, wherein each of said right and left mandible engaging sections comprises:
   a) an adjustable and angled airway opening member configured to engage a corresponding mandible angle of the subject and to assure opening of the airway;
   b) a substantially planar baseplate pivotally connected to said occipital portion; and
   c) a carrier for said adjustable and angled airway opening member which is incrementally and anteroposteriorly displaceable along a groove formed in said baseplate,
   wherein said adjustable and angled airway opening member protrudes medially from said baseplate and comprises a first element configured to contact a bottom of the mandible angle, and a second element which is angularly spaced from said first element, said second element extending upwardly and posteriorly from only a posterior end of said first element to define an obtuse angle between said first and second elements having an unoccupied interior space,
   wherein said adjustable and angled airway opening member, when displaced anteriorly along said groove, is configured to receive within said interior space the corresponding mandible angle proximate to a junction with a ramus and to apply a force onto the corresponding mandible angle, for causing jaws of the subject to open.

2. The cervical collar according to claim 1, wherein said occipital portion and said separate right and left sternum engaging portions are formed in a single panel.

3. The cervical collar according to claim 1, wherein the single panel is of bilateral symmetry and is capable of being flattened out.

4. The cervical collar according to claim 3, wherein the single panel is configured with two portions contiguous with a corresponding sternum engaging portion and between which the occipital portion is interposed, for engaging, when tensioned, a sternocleidomastoid muscle (SCM) of the subject, to prevent sideways head movement.

5. The cervical collar according to claim 4, wherein each of the separate right and left sternum engaging portions is defined by an L-shaped, laterally extending edge extending from a convex upper edge of a corresponding sternocleidomastoid muscle (SCM) portion, and by a concave lower edge of said corresponding SCM portion.

6. The cervical collar according to claim 5, wherein the concave lower edge of the corresponding SCM portion extends continuously from a convex lower edge of the occipital portion to a convex lower edge of the respective sternum engaging portion, and a convex upper edge of the respective sternum engaging portion extends continuously from the corresponding L-shaped edge.

7. The cervical collar according to claim 6, wherein the convex lower edge of the occipital portion has a significantly greater curvature than a convex upper edge of the occipital portion which is continuous with the convex upper edge of the corresponding SCM portion, and each of the right and left sternum engaging portions is considerably thinner than the corresponding SCM portion.

8. The cervical collar according to claim 3, wherein said separate right and left sternum engaging portions have bilateral symmetry and are simultaneously tensionable and fastenable together to ensure symmetric and stable fixation at a sternum of the subject while being configured to maintain an anterior triangle of a neck of the subject in an unobstructed condition, thereby facilitating monitoring of various throat related clinical conditions following a traumatic event.

9. The cervical collar according to claim 1, wherein the carrier is ratchetedly displaceable along the groove, and is connected to a manipulator by a fastening element passing through the groove.

10. The cervical collar according to claim 9, wherein the manipulator protrudes distally from the baseplate.

11. The cervical collar according to claim 1, wherein each of the right and left mandible engaging sections is pivotal about a corresponding axle fixed to the occipital portion in order to facilitate engagement with a mandible of the subject.

12. The cervical collar according to claim 1, wherein the carrier is controllably displaceable along the groove formed in said baseplate.

13. The cervical collar according to claim 1, wherein the first and second elements are angularly spaced by the obtuse angle which ranges from 110 to 160 degrees.

14. The cervical collar according to claim 1, further comprising right and left straps attachable to an anterior portion of a corresponding baseplate, wherein said right and left straps are simultaneously tensionable and fastenable together on a chin of the subject to ensure symmetric stabilization.

15. The cervical collar according to claim 1, wherein a distance between an upper edge and a lower edge of the occipital portion is sufficiently great to ensure that said lower edge is capable of contacting a back of the subject, to prevent rearward head motion upon application of a tensile force to a top of the occipital portion by the right and left mandible engaging sections and the separate right and left sternum engaging portions.

16. The cervical collar according to claim 1, wherein the first element of the adjustable and angled airway opening member, is substantially parallel to a bottom edge of the baseplate and the second element is positioned in a posterior region of the carrier.

17. The cervical collar according to claim 1, further comprising a corresponding sagitally oriented axle fixed to the occipital portion about which the baseplate is pivotable in order to facilitate engagement with the mandible.

* * * * *